United States Patent
Lattner et al.

(10) Patent No.: US 6,844,480 B2
(45) Date of Patent: Jan. 18, 2005

(54) METHOD OF SEPARATING DIMETHYL ETHER FROM AN OLEFIN STREAM

(75) Inventors: James R. Lattner, Seabrook, TX (US); David R Lumgair, Jr., Craddockville, VA (US); Jeffrey A. Kabin, Houston, TX (US); Michael Peter Nicoletti, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 397 days.

(21) Appl. No.: 10/184,389

(22) Filed: Jun. 27, 2002

(65) Prior Publication Data
US 2003/0004386 A1 Jan. 2, 2003

Related U.S. Application Data
(60) Provisional application No. 60/302,462, filed on Jul. 2, 2001.

(51) Int. Cl.[7] .............................. C08F 10/06; C07C 7/08
(52) U.S. Cl. ........................ 585/833; 585/836; 585/639; 585/864; 585/868; 203/95; 203/96; 526/77; 208/311; 208/313; 208/321; 208/347
(58) Field of Search ................................ 585/833, 836, 585/639, 864, 868; 203/95, 96; 208/311, 313, 347

(56) References Cited

U.S. PATENT DOCUMENTS

| | | | |
|---|---|---|---|
| 4,387,263 A | 6/1983 | Vogt et al. .................. 585/640 |
| 4,474,647 A | 10/1984 | Asselineau et al. ........... 203/49 |
| 4,499,327 A | 2/1985 | Kaiser ......................... 585/640 |
| 4,603,225 A | * 7/1986 | Colaianne et al. .......... 568/697 |
| 4,777,321 A | 10/1988 | Harandi et al. .............. 585/640 |
| 4,802,956 A | 2/1989 | Dornhagen et al. ........... 203/42 |
| 5,028,400 A | 7/1991 | Harandi et al. .............. 422/211 |
| 5,041,690 A | 8/1991 | Harandi et al. .............. 568/695 |
| 5,090,977 A | 2/1992 | Strack et al. .................. 62/23 |
| 5,122,236 A | 6/1992 | Smith, Jr. et al. ............. 203/43 |
| 5,146,032 A | 9/1992 | Harandi ...................... 585/640 |
| 5,510,566 A | 4/1996 | Muoio et al. ................ 585/824 |
| 5,609,734 A | * 3/1997 | Streicher et al. .............. 203/39 |
| 5,679,872 A | 10/1997 | Streicher .................... 568/699 |
| 5,750,799 A | 5/1998 | van Dijk .................... 568/698 |
| 5,811,621 A | 9/1998 | van Dijk .................... 585/639 |
| 5,817,906 A | 10/1998 | Marker et al. .............. 585/640 |
| 5,914,433 A | * 6/1999 | Marker ....................... 585/313 |
| 5,990,369 A | 11/1999 | Barger et al. ............... 585/640 |
| 6,121,504 A | 9/2000 | Kuechler et al. ............ 585/640 |
| 6,559,248 B2 | * 5/2003 | Hendriksen et al. .......... 526/77 |
| 6,740,791 B2 | * 5/2004 | Kuechler et al. ............ 585/639 |

* cited by examiner

Primary Examiner—Walter D. Griffin
Assistant Examiner—Tam M. Nguyen (57) ABSTRACT

This invention is directed to a method of removing dimethyl ether from an olefin stream. Dimethyl ether is removed from the olefin stream by first separating the olefin stream into a first stream comprising dimethyl ether and lighter boiling point compounds, and a second stream comprising $C_4+$ olefin and higher boiling point hydrocarbons. The dimethyl ether is then separated from the first stream using extractive distillation.

32 Claims, 2 Drawing Sheets

METHOD OF SEPARATING DIMETHYL ETHER FROM AN OLEFIN STREAM

This application claims the benefit of U.S. Provisional No. 60/302,462 filed Jul. 2, 2001.

FIELD OF THE INVENTION

This invention is directed to a method of removing oxygenated contaminants from an olefin stream. In particular, this invention is directed to an method of removing dimethyl ether from an olefin stream.

BACKGROUND OF THE INVENTION

Olefins, particularly ethylene and propylene, are desirable as a feed source for making derivative products such as oligomers, e.g., higher olefins, and polymers such as polyethylene and polypropylene. Olefin feed sources have traditionally been produced by cracking petroleum feedstocks.

U.S. Pat. No. 5,090,977 discloses a method of making olefins by steam cracking. The method includes separating the olefin product into methane, hydrogen, ethane, ethylene, propylene and $C_5+$ streams. The disclosed separation preferentially produces propylene, and no propane, butane, butene, or butadiene streams are produced.

Oxygenate feed stocks, however, are becoming an alternative to petroleum feed stocks for making olefins, particularly large quantities of ethylene and propylene for the production of higher olefins and plastic materials. In general, the olefins are formed by contacting the oxygenate components with a molecular sieve catalyst to catalytically convert the oxygenates to olefins.

For example, U.S. Pat. No. 4,499,327, discloses a process for making olefins from methanol using any of a variety of silicoaluminophosphate (SAPO) molecular sieve catalysts. The process is carried out at a temperature between 300° C. and 500° C., a pressure between 0.1 atmosphere to 100 atmospheres, and a weight hourly space velocity (WHSV) of between 0.1 and 40 $hr^{-1}$. The process is highly selective for making ethylene and propylene.

U.S. Pat. No. 6,121,504 also discloses a method of making olefin product from oxygenate feed using molecular sieve catalysts. Water and other unwanted by-products are removed from the olefin product by contacting with a quench medium. After contacting with the quench medium, a light product fraction is obtained which comprises the desired olefins, but also includes dimethyl ether, methane, CO, $CO_2$, ethane, propane, and other minor components such as water and unreacted oxygenate feedstock.

In order to further process olefins, it is often necessary to reduce or remove the amount of undesirable hydrocarbon by-products that are present in the olefin composition. This is because derivative manufacturing processes may use catalysts that are quite sensitive to the presence of certain hydrocarbons. For example, dimethyl ether has been found to act as a poison to certain catalysts.

U.S. Pat. No. 4,474,647 discloses that dimethyl ether can adversely impact the oligomerization of certain olefins. The patent describes a process for removing dimethyl ether from a $C_4$ and/or $C_5$ olefin stream using distillation. The stream is distilled and separated into an overhead and a bottoms stream. The overhead stream contains dimethyl ether, water, and various hydrocarbons, and the bottoms stream contains purified olefins.

U.S. Pat. No. 5,609,734 discloses a method of removing methanol and dimethyl ether from a mixed hydrocarbon stream. The hydrocarbon stream containing the methanol and dimethyl ether is distilled such that the dimethyl ether and methanol are removed in an overhead stream. Additional methanol is recovered in a side stream, in which a methanol permeable membrane is used to obtain the additional separation. Purified hydrocarbon is removed from an bottoms stream.

U.S. Pat. No. 4,387,263 discloses a method of making olefins from methanol using a zeolite catalyst. The methanol is contacted with the catalyst in a reactor to form an olefin product containing $C_2$ to $C_4$ olefins, water, unreacted methanol, and dimethyl ether, which is considered an intermediate product. The $C_2$ to $C_4$ olefins are separated from the water, unreacted methanol and dimethyl ether. The unreacted methanol and the dimethyl ether are then stripped from the water, and recycled to the reactor.

U.S. Pat. No. 4,603,225 discloses a method of making methyl tertiary butyl ether (MTBE) by reacting isobutylene with methanol in the presence of a catalyst. The MTBE is recovered by distillation, which also produces a raffinate stream. The raffinate stream contains unreacted olefins and methanol, water, and dimethyl ether. The dimethyl ether is washed from the raffinate stream using a methanol and water wash.

Removal of dimethyl ether from olefin streams is particularly difficult, since very low levels of dimethyl ether can act as catalyst poisons. This means olefin streams such as ethylene and propylene should contain little if any dimethyl ether, if further catalytic processing of the olefin stream is desired. Therefore, it is highly desirable to find additional methods of removing dimethyl ether from olefin streams.

SUMMARY OF THE INVENTION

This invention provides a method for removing oxygenated contaminants such as dimethyl ether from an olefin stream. It is desirable to remove such oxygenated components, since they may poison catalysts that are used to further process such olefins, particularly ethylene and propylene.

The invention provides, in one embodiment, a method of separating dimethyl ether from an olefin stream. The method comprises separating the olefin stream into a first stream comprising dimethyl ether and lighter boiling point olefin compounds, and a second stream comprising $C_4+$ olefin and higher boiling point hydrocarbons. The dimethyl ether present in the first stream is then separated using extractive distillation. Desirably, the olefin stream is separated into the first and second streams using distillation.

In another embodiment, the first stream comprises ethylene, and the ethylene is separated from the overhead stream prior to separating the dimethyl ether using the extractive distillation. Desirably, the extractive distillation is carried out in a column having a rectification zone and a stripping zone. In one preferred embodiment, the extractive distillation column has a feed location for introducing the olefin stream into the column such that the rectification zone is above the feed location and the stripping zone is below the feed location.

It is desirable in the invention that the extractive distillation uses a polar extractant having an average boiling point of at least 100° F. (38° C.) at 1 atm. In general, it is also desirable that the first stream comprises not greater than about 5 wt % $C_4+$ olefin and higher boiling point hydrocarbons, and the second stream comprises at least about 60 wt % $C_4+$ olefin and higher boiling point hydrocarbons.

In still another embodiment of the invention, the first stream comprises ethylene, and the ethylene is separated from the first stream and polymerized to form polyethylene. In an alternative embodiment, the first stream comprises propylene, and the propylene is separated from the first stream and polymerized to form polypropylene.

Also provided in this invention is a method of separating dimethyl ether from an olefin stream, which comprises providing an olefin stream containing ethylene, propylene, dimethyl ether and $C_4+$ olefin and higher boiling point hydrocarbons, with the olefin stream being provided from any conventional source. The olefin stream is separated into a first stream comprising the ethylene, propylene and dimethyl ether and a second stream comprising the $C_4+$ olefin and higher boiling point hydrocarbons. The dimethyl ether present in the first stream is then separated using extractive distillation.

The invention also provides a method of removing dimethyl ether from an olefin stream made from an oxygenate to olefin reaction process, which comprises contacting the oxygenate with a molecular sieve catalyst to form an olefin stream, wherein the olefin stream comprises ethylene, propylene, dimethyl ether and $C_4+$ olefin and higher boiling point hydrocarbons. The olefin stream is separated into a first stream comprising the ethylene, propylene and dimethyl ether and a second stream comprising the $C_4+$ olefin and higher boiling point hydrocarbons. The dimethyl ether present in the first stream is then separated using extractive distillation.

Further provided in this invention is a method of removing dimethyl ether from an olefin stream made from an oxygenate to olefin reaction process which comprises contacting oxygenate with a molecular sieve catalyst to form an olefin stream. The olefin stream is distilled to separate a propane and dimethyl ether containing stream from the olefin stream, wherein the propane and dimethyl ether containing stream comprises not greater than 5 wt % $C_4+$ olefin and higher boiling point hydrocarbons. The dimethyl ether present in the propane and dimethyl ether containing stream is then separated using extractive distillation.

BRIEF DESCRIPTION OF THE DRAWINGS

Examples of various embodiments of this invention are shown in the attached Figures, wherein.

DETAILED DESCRIPTION OF THE INVENTION

Olefins are typically used as feedstreams for forming a variety of end products. One example is ethylene and propylene, which can be used, inter alia, to make plastic materials such as polyethylene and polypropylene.

Often, olefin streams that are to be used as feedstreams for further processing contain contaminants. An example of one type of contaminant is oxygenated hydrocarbon compounds. There compounds are hydrocarbons that contain at least one oxygen atom.

Many oxygenated hydrocarbon contaminants that are found in olefin streams are water soluble, and can, therefore, be removed using a water washing system. However, some oxygenated hydrocarbon contaminants are not very water soluble, and will not be removed using water alone. One such example is dimethyl ether.

In this invention, dimethyl ether is removed from an olefin stream by first separating the olefin stream into one or a first stream comprising dimethyl ether and lighter boiling point compounds, and a second stream comprising $C_4+$ olefin and higher boiling point hydrocarbons. Separation into such streams can be by any means. Distillation is one example. The dimethyl ether is then separated from the first stream by extractive distillation, which is essentially a distillation process that incorporates the use of an extractant to aid in the distillation process.

The olefin streams from which the dimethyl ether is removed according to this invention, can be provided from any source. For example, the olefins can come from by the cracking of hydrocarbons, such as ethane, propane, butane, naphtha and gas oil, dehydrogenation of paraffins, metathesis reactions of other olefins, catalytic cracking and deep catalytic cracking of hydrocarbons.

Although the olefin stream can be provided by any conventional source which contains dimethyl ether, the invention is particularly suited to removing dimethyl ether from olefin streams made from an oxygenate to olefin process. In one embodiment of this invention, an olefin stream containing dimethyl ether is obtained by contacting oxygenate feedstock with a molecular sieve catalyst.

In a preferred embodiment of the process of the invention, the oxygenate feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

Molecular sieves capable of converting an oxygenate to an olefin compound include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between –2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,- 295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 $\mu$m to about 0.6 $\mu$m with a D90 particle size distribution of less than about 1 $\mu$m.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system. The reactor system preferably is a fluid bed reactor system having a first reaction zone within one or more riser reactor (s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr$^{-1}$ to about 20,000 hr$^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1,000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, is not critical. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol and dimethyl ether is in the range of from about 20 hr$^{-1}$ to about 300 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 hr$^{-1}$ to about 100 hr$^{-1}$, at a temperature of from about 350° C. to 550° C., and silica to Me$_2$O$_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

The oxygenate to olefin process forms a substantial amount of water as a by-product. Much of this water can be removed by cooling the olefin stream from the oxygenate reactor to a temperature below the condensation temperature of the water in the stream. Preferably, the temperature of the product stream is cooled to a temperature below the condensation temperature of the oxygenate feed for the oxygenate to olefins process. In certain embodiments, it is desirable to cool the product stream below the condensation temperature of methanol.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing, heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column.

In one particular embodiment of the invention, the quenched olefin stream is further processed by compression, preferably multi-staged compression. Two, three, four or more stages can be used, with two or three stages being preferred.

In another embodiment of the invention, the olefin stream is compressed to a pressure that is greater than that at which the oxygenate to olefin reaction process is carried out. Preferably, the olefin stream is compressed to a pressure of at least about 30 psia (207 kPa), more preferably at least about 50 psia (345 kPa), most preferably at least about 100 psia (689 kPa). High pressure ranges are particularly preferred, with the upper limit being a practical one based on cost of design and ease of operation. Practical high pressure limits are generally considered to be up to about 1,000 psia (6,895 kPa), with lower limits of about 750 psia (5,171 kPa), about 500 psia (3,447 kPa), and about 400 psia (2,758 kPa) being increasingly preferred.

In one embodiment of this invention, the provided olefin stream from which the dimethyl ether is to be removed comprises not greater than about 15,000 wppm water so as to minimize clathrate and/or free water formation in the distillation column in which the olefin stream containing the dimethyl ether is separated from the $C_4+$ olefin and higher boiling point containing hydrocarbon stream. Preferably the provided olefin stream contains not greater than about 10,000 wppm water, more preferably not greater than 5,000 wppm water, and most preferably not greater than about 1,000 wppm water.

It is not necessary in this invention that the provided olefin stream be completely dry. That is, the olefin stream can contain some water. The benefit of the olefin stream containing some amount of water is that additional and/or complex drying equipment will not be needed before separating the dimethyl ether containing stream from the $C_4+$ olefin and higher boiling point hydrocarbon containing stream. Preferably, the provided olefin stream contains at least about 10 wppm water, more preferably at least about 100 wppm water, and most preferably at least about 200 wppm water.

In another embodiment of the invention, the provided olefin stream from which the dimethyl ether is to be removed is low in methanol so as to make separation of the $C_4+$ olefin and higher boiling point hydrocarbons from the dimethyl ether containing stream easier. Desirably, the provided olefin stream contains not greater than about 5 wt % methanol. Preferably, the provided olefin stream contains not greater than about 2 wt % methanol, more preferably not greater than about 1 wt % methanol, most preferably not greater than about 0.5 wt % methanol. The methanol content can be controlled when the olefin stream is provided from an oxygenate to olefin process, for example, by appropriate adjustment of conversion and/or quenching conditions.

In this invention, a $C_4+$ olefin and higher boiling point stream, which is comprised of a majority of 1-butene and higher boiling point compounds (such compounds including 1-butene and any hydrocarbon having a boiling point higher than that of 1-butene, including hydrocarbons having less than 4 carbons) is desirably separated from the provided olefin stream prior to removing the dimethyl ether. Any conventional separation process can be used. Distillation is preferred. In such a case, distillation temperature is controlled so that the dimethyl ether is removed in one stream along with lighter boiling point hydrocarbons, and the $C_4+$ olefin and higher boiling point compounds would be removed as a separate stream.

In one embodiment of the invention, a $C_4+$ olefin and higher boiling point steam is separated as a separate or second stream, and comprises at least about 50 wt % $C_4+$ olefin and higher boiling point compounds. Preferably, the $C_4+$ olefin and higher boiling point stream comprises at least about 60 wt % $C_4+$ olefin and higher boiling point compounds, more preferably at least about 70 wt % $C_4+$ olefin and higher boiling point compounds.

In another embodiment of the invention, the second stream comprises not greater than about 30 wt % $C_3-$ olefin and lighter boiling point components, $C_3-$ olefin and lighter boiling point components being considered propylene and any hydrocarbon compound having a boiling point less than propylene. Preferably, the $C_3-$ olefin and lighter boiling point stream comprises not greater than about 20 wt % $C_3-$ and lighter boiling point compounds, more preferably not greater than about 15 wt % $C_3-$ and lighter boiling point compounds.

In one embodiment of the invention, the dimethyl ether in the separated olefin stream is removed from the olefin portion of the stream using extractive distillation. The olefin stream containing the dimethyl ether can comprise predominantly ethylene and propylene, preferably at least about 50 wt % ethylene and propylene, more preferably at least about 60 wt % ethylene and propylene, and most preferably at least about 70 wt % ethylene and propylene.

In another embodiment on the invention, the ethylene is separated from the olefin stream prior to extractive distillation. Such separation can be by any conventional means. Distillation is preferred. When ethylene is separated from the olefin stream prior to extractive distillation, the resulting olefin stream desirably contains at least about 70 wt % propylene, preferably at least about 80 wt % propylene, more preferably at least about 90 wt % propylene.

The olefin stream that contains the dimethyl ether that is to be removed by extractive distillation is low in $C_4+$ olefin and higher boiling point components to provide for easier removal of the dimethyl ether. In one embodiment of the invention, the olefin stream comprises not greater than about 5 wt % $C_4+$ olefin and higher boiling point components. Preferably, the olefin stream comprises not greater than about 2 wt % $C_4+$ olefin and higher boiling point components, more preferably not greater than about 1 wt % $C_4+$ olefin and higher boiling point components.

Oxygenate contaminants can be removed to very low quantities in an olefin stream using an extractive distillation process under the appropriate conditions and with an appropriate extractant. Extractive distillation differs from a wash or conventional distillation process in that olefin is distilled from the contaminant using an extractant to aid the distillation process.

Extractive distillation is typically carried out using a vessel or tower having internal packing or trays that creates a temperature difference from top to bottom of the tower. The upper portion of the tower is the cooler portion, and higher volatile components in the olefin exit from the top of the tower.

The location of the feed point of the extractant relative to the hydrocarbon feed point in the extractive distillation column can be adjusted for optimal results. In one embodiment of the invention, however, the extractive distillation has a rectification and stripping zone. It a preferred embodiment, the rectification zone is located above the hydrocarbon feed location, which will aid in keeping methanol and dimethyl ether out of the overhead hydrocarbon product stream. In another preferred embodiment, the stripping zone is located below the hydrocarbon feed point, which will aid in keeping propane out of the bottoms stream which contains dimethyl ether and extractant.

In one embodiment, extractive distillation is carried out at an overhead column pressure of at least about 120 psia (827 kPa). Preferably, extractive distillation is carried out at an overhead column pressure of at least about 150 psia (1034 kPa), more preferably at least about 175 psia (1026 kPa), and most preferably at least about 200 psia (1378 kPa).

It is desirable to maintain higher top stage temperatures in the extractive distillation column to avoid clathrate or free water formation. The greater the content of the methanol in the top stage, however, the lower the temperature can be, since the presence of methanol will inhibit clathrate or free water formation. In one embodiment of the invention, the top stage temperature is at least about 10° F. (−12° C.). Preferably, the top stage temperature is at least about 20° F. (−7° C.), more preferably at least about 30° F. (−1° C.), and most preferably at least about 40° F. (4° C.)

An extractant or solvent is added to the extractive distillation vessel or tower, preferably in a quantity to enhance or suppress the volatility of the oxygenate relative to the olefin. This makes it easier to distill the oxygenate from the olefin, resulting in removal of the oxygenate to very low levels. In one embodiment, the extractant is added to the extractive distillation vessel at a molar ratio of extractant to total hydrocarbon feed of from about 4:1 to about 1:1; preferably from about 3:1 to about 1.2:1; and about 1.5:1.

Extractants which can be used in this invention are liquids at 1 atm. These exactants also desirably have an average boiling point of at least 100° F. (38° C.), preferably at least 120° F. (49° C.), and more preferably at least 150° F. (66° C.), each boiling point stated at 1 atm. Average boiling point, as defined herein, takes into account the boiling point of each compound in the extractant on a weight average basis. For example, an extractant containing 90 wt. % of a compound having a boiling point of 100 degrees and 10 wt. % of a compound having a boiling point of 200 degrees would have an average boiling point of 110 degrees.

The extractants are also desirably polar compositions. Such compositions preferably contain compounds such as water, monohydric alcohols, polyhydric alcohols, or mixtures thereof. Preferred monohydric alcohols include ethanol and propanol. Preferred polyhydric alcohols include glycols. Preferred glycols include ethylene glycol and tri-ethylene glycol. It is desirable that the extractant contain at least about 75 wt. % water, monohydric alcohol, and or polyhydric alcohol, preferably at least about 85 wt. %, more preferably at least about 90 wt. %, and most preferably at least about 95 wt. %. Water is most preferred as the extractant.

The extractive distillation vessel or column can be of conventional design. Examples include a packed distillation column and a column containing trays.

The extractive distillation process is desirably operated at a pressure higher than the quench operating pressure. Preferably extractive distillation is carried out at an operating pressure of at least about 50 psi (345 kPa) higher than the quench, more preferably at least about 100 psi (689 kPa), and most preferably at least about 150 psi (1034 kPa) higher. Preferably, the extractive distillation process is carried out at a pressure of from about 100 psia (689 kPa) to about 5000 psia (34,474 kPa). More preferred operating ranges are from about b 150psia (1034 kPa) to about 4000 psia (27,579 kPa); about 200 psia (1379 kPa) to about 3000 psia (20,684 kPa); about 250 psia (1,724 kPa) to about 2500 psia (17,237 kPa); and about 300 psia (2,068 kPa) to about 2000 psia (13,790 kPa). As the pressure in the extractive distillation vessel increases, the more oxygenate, particularly dimethyl ether, is removed from the olefin stream.

The extractive distillation process is particularly effective for removing very low concentrations of dimethyl ether present in an olefin stream. It is a very efficient process for removing dimethyl ether from an olefin stream which contains not greater than 20 wt. % dimethyl ether. Extractive distillation carried out according to this invention is even effective with olefin streams containing not greater than 10 wt. %, 5 wt. %, 1 wt. %, 0.5 wt. % or 0.1 wt. % dimethyl ether.

In one embodiment of the invention, extractant is added to the top of an extractive distillation column, and is removed as a lower or bottoms product from the bottom of the extractive distillation column. The extractive distillation column is desirably operated below the boiling point of the extractant, and above the boiling point of the product effluent at the operating pressure of the distillation column. As the extractant travels down the distillation column, dimethyl ether is absorbed into the extractant, and removed along with the extractant as a liquid bottoms product from the extractive distillation column.

The extractive distillation process of this invention allows for the recovery of an olefin product having very low dimethyl ether levels. The total dimethyl ether content of the ethylene and/or propylene product streams, particularly an olefin stream containing at least 50 wt. % ethylene and/or propylene is generally not greater than about 5000 wt. ppm dimethyl ether. Ethylene and/or propylene streams containing not greater than about 3000 wt. ppm, 2000 wt. ppm, 1000 wt. ppm, 500 wt. ppm, 250 wt. ppm, 100 wt. ppm, 50 wt. ppm, 10 wt. ppm and 5 wt. ppm dimethyl ether are also readily achievable.

At least a majority (i.e., 50%) of the dimethyl ether entering the extractive distillation column is recovered in the lower or bottoms stream of the extractive distillation column which contains the extractant. Preferably, at least about 75%; more preferably, at least about 85%; and most preferably, at least about 95% of the dimethyl ether entering the extractive distillation column is recovered along with the extractant.

The dimethyl ether contained in the extractant leaving the extractive distillation column can be recovered and used after a regeneration process. Regeneration of the extractant can be accomplished by conventional means. Preferably, the extractant is regenerated by separating the extractant from absorbed compounds in a distillation column. Preferably, an extractant that has a boiling point temperature at least about 5° F. (3° C.), more preferably at least about 10° F. (6° C.) higher, than the absorbed compounds is used in the extractive distillation column.

The bottoms product from the extractive distillation column is fed into the distillation column for regeneration. The distillation column produces an overhead stream comprising oxygenates and hydrocarbons that were absorbed by the extractant in the extractive distillation column. The bottoms product from the distillation column is regenerated extractant that can be returned to the extractive distillation column.

Preferably, the extractant is cooled before being returned to the top of the extractive distillation column. Cooling the extractant below the temperature of the extractive distillation column's overhead product stream aids the efficiency of the column. In an extractive distillation column using water as the extractant, preferably the temperature of the extractant is cooled to below about 95° F. (35° C.), and more preferably the extractant is cooled to below about 90° F. (32° C.), before being returned to the extractive distillation column. The extractant can be cooled by conventional means.

If methanol is used as the extractant, the dimethyl ether containing extractant can be combined with an oxygenate stream that is used to feed an oxygenate to olefins reaction system. The dimethyl ether and the methanol will readily react with the catalyst in such a system.

The ethylene and propylene streams treated and separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455;

3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefin compounds, particularly the butenes in the $C_4+$ olefin and higher boiling point stream separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butenes in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

Figure 1:
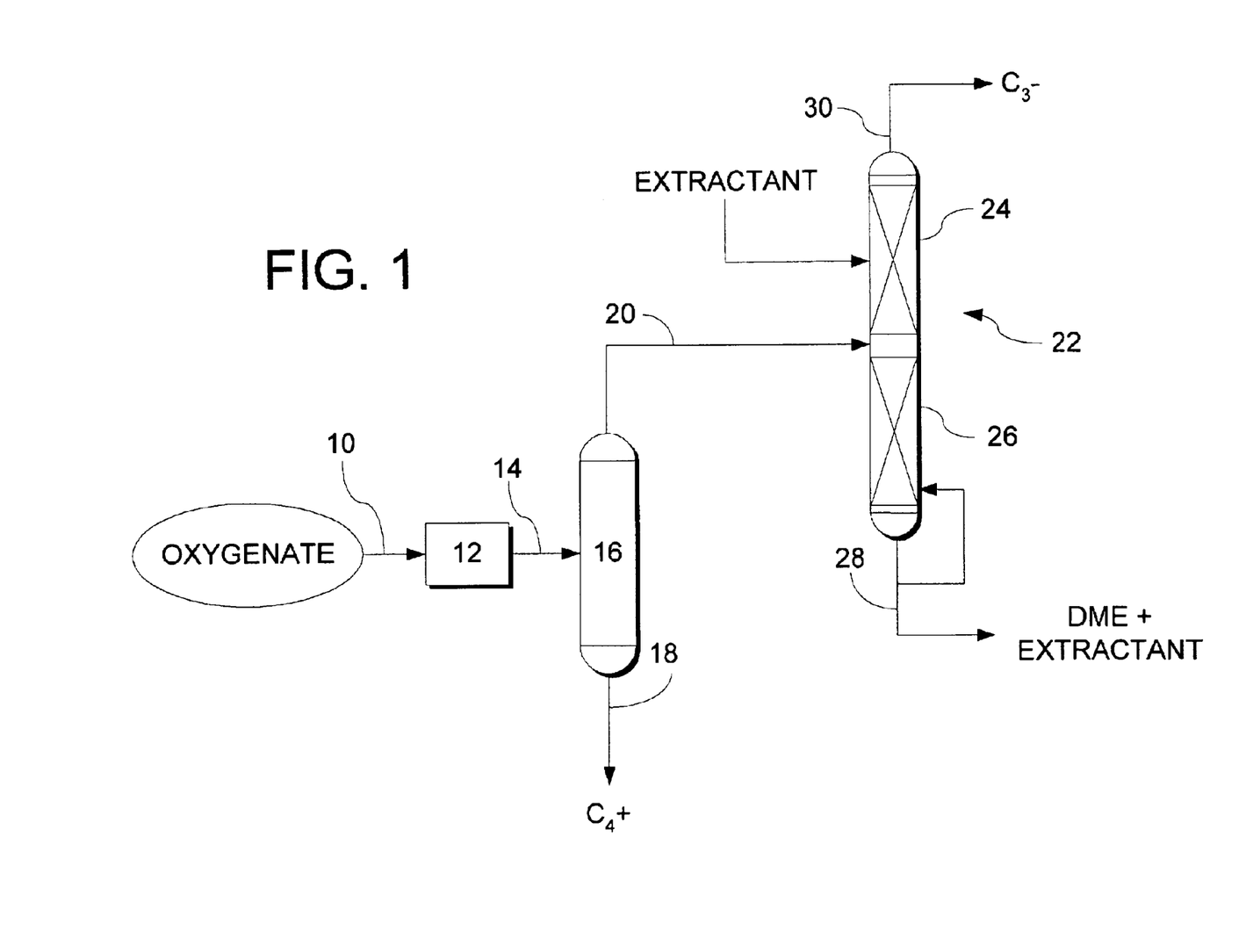
FIG. 1 is a flow diagram showing one scheme of separating dimethyl ether from an olefin stream containing a majority of $C_3-$ olefin and lighter boiling point components.

Examples of separating dimethyl ether from olefin streams are shown in the Figures. In FIG. 1, oxygenate is sent through a line 10 to an oxygeante to olefin reaction system 12. The olefin reaction system includes an oxygenate to olefin reactor which converts the oxygenate to olefin, and a quench and compression system which removes a significant portion of the water by-product formed in the oxygenate to olefin reaction.

Olefin from the olefin reaction system 12 is sent through a line 14 to a distillation process 16 where $C_4+$ olefins and higher boiling point components are separated from the olefin. The $C_4+$ olefins and higher boiling point components leave the distillation process as a bottoms stream though a line 18, and light olefins (i.e., $C_2$ and $C_3$ olefins), with little if any remaining $C_4+$ olefins and higher boiling point components, leave the distillation process 16 as an overhead stream through a line 20 to an extractive distillation column 22. The extractive distillation column has a rectification zone 24 above the hydrocarbon feed location, and a stripping zone 26 located below the hydrocarbon feed point.

An extractant is fed to the top portion of the extractive distillation column 22 to extract dimethyl ether contained in the olefin overhead stream from line 20. The dimethyl ether and extractant leave the extractive distillation column through a bottoms line 28. A portion of the material in the bottoms line 28 is heated using a heating system, e.g., heat exchanger, (not shown) and recycled back to the extractive distillation column 22.

A $C_3$– olefin and lighter boiling point hydrocarbon containing stream leaves the extractive distillation column 22 as an overhead stream through a line 30. The $C_3$– olefin and lighter boiling point hydrocarbon containing stream is subsequently separated into ethylene and propylene streams, and contains substantially no dimethyl ether.

Figure 2:
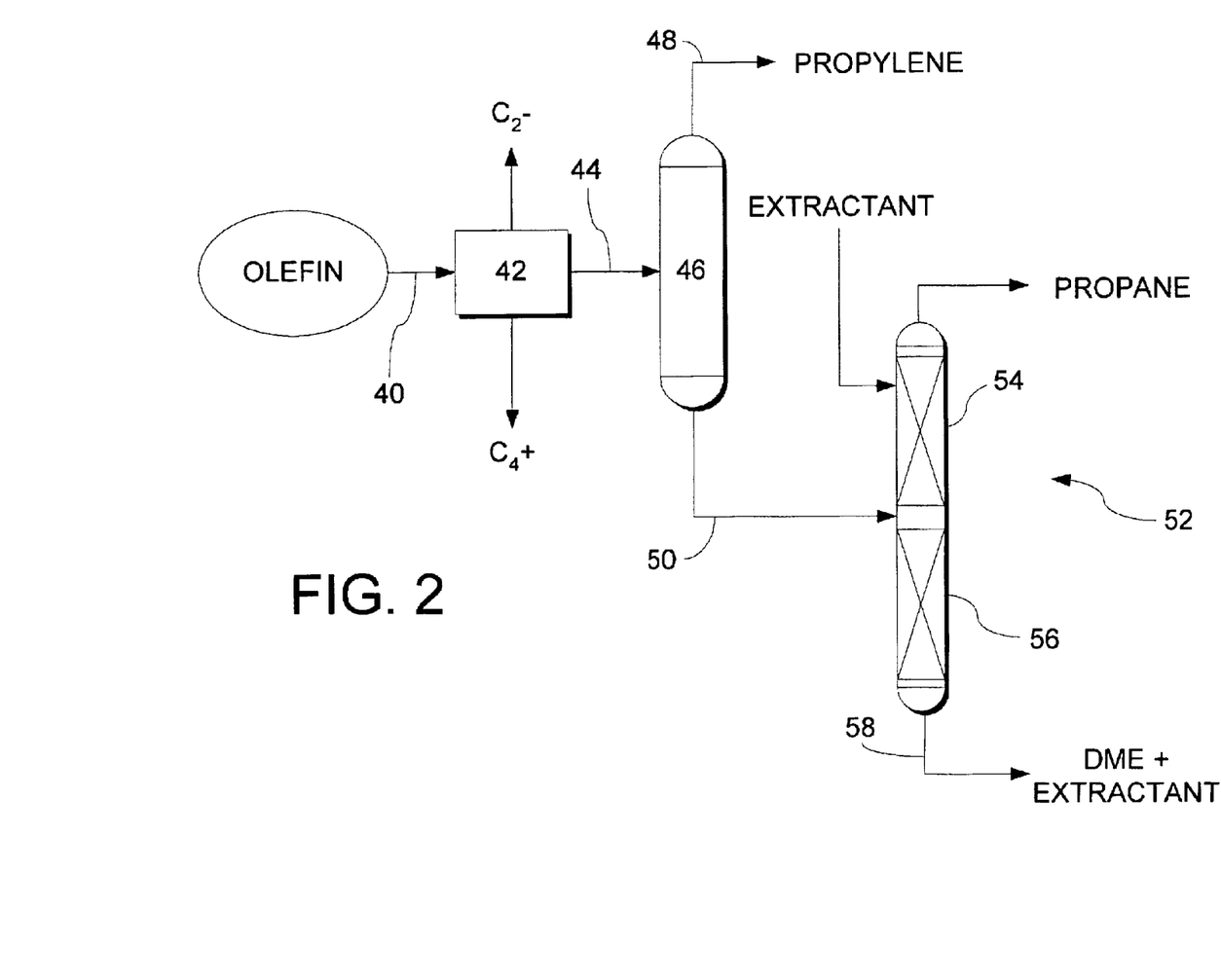
FIG. 2 is a flow diagram showing another scheme of separating dimethyl ether from an olefin stream containing a majority of propylene and propane.

Another example of separating dimethyl ether is shown in the FIG. 2. In FIG. 2, an olefin stream is sent through a line 40 to a fractionation system 42. The fractionation system 42 separates a $C_2$– olefin and lighter boiling point hydrocarbon containing stream and a $C_4+$ olefin and higher boiling point stream from the olefin stream, leaving dimethyl ether in a $C_3$ stream in line 44 which contains a substantial portion of propylene, along with propane. The olefin stream comprising the dimethyl ether is sent through a line to a separator 46, where propylene is separated as an overhead stream, and leaves the separator 46 through a line 48. A bottoms stream leaves the separator 46 through a line 50. The bottoms stream contains a substantial amount of propane and dimethyl ether.

The bottoms stream leaving the separator 46 through the line 50 is sent to an extractive distillation column 52. The extractive distillation column has a rectification zone 54 above the hydrocarbon feed location, and a stripping zone 56 located below the hydrocarbon feed point.

An extractant is fed to the top portion of the extractive distillation column 52 to extract dimethyl ether contained in the bottoms stream containing the propane. The dimethyl ether and extractant leave the extractive distillation column through a bottoms line 58. A portion of the material in the bottoms line 58 is heated using a heating system, e.g., heat exchanger, (not shown) and recycled back to the extractive distillation column 52.

Having now fully described this invention, it will be appreciated by those skilled in the art that the invention can be performed within a wide range of parameters within what is claimed, without departing from the spirit and scope of the invention.

What is claimed is:

1. A method of separating dimethyl ether from an olefin stream, comprising:
    separating the olefin stream into a first stream comprising dimethyl ether and lighter boiling point olefin compounds, and a second stream comprising $C_4+$ olefin and higher boiling point hydrocarbons; and
    separating the dimethyl ether present in the first stream using extractive distillation.

2. The method of claim 1, wherein the olefin stream is separated into the first and second streams using distillation.

3. The method of claim 1, wherein the first stream comprises ethylene, and the ethylene is separated from the first stream prior to separating the dimethyl ether using the extractive distillation.

4. The method of claim 1, wherein the extractive distillation is carried out in a column having a rectification zone and a stripping zone.

5. The method of claim 4, wherein the column has a feed location for introducing the olefin stream into the column such that the rectification zone is above the feed location and the stripping zone is below the feed location.

6. The method of claim 1, wherein the extractive distillation uses a polar extractant having an average boiling point of at least 100° F. (38° C.) at 1 atm.

7. The method of claim 1, wherein the first stream comprises not greater than 5 wt % $C_4+$ olefin and higher boiling point hydrocarbons, and the second stream comprises at least 60 wt % $C_4+$ olefin and higher boiling point hydrocarbons.

8. The method of claim 1, wherein the first stream comprises ethylene, and the ethylene is separated from the first stream and polymerized to form polyethylene.

9. The method of claim 1, wherein the first stream comprises propylene, and the propylene is separated from the first stream and polymerized to form polypropylene.

10. A method of separating dimethyl ether from an olefin stream, comprising:

provided an olefin stream comprising ethylene, propylene, dimethyl ether and $C_4+$ olefin and higher boiling point hydrocarbons;

separating the olefin stream into a first stream comprising the ethylene, propylene and dimethyl ether and a second stream comprising the $C_4+$ olefin and higher boiling point hydrocarbons; and separating the dimethyl ether present in the first stream using extractive distillation.

11. The method of claim 10, wherein the olefin stream is separated into the first and second streams using distillation.

12. The method of claim 10, wherein the ethylene is separated from the first stream prior to separating the dimethyl ether using the extractive distillation.

13. The method of claim 10, wherein the extractive distillation is carried out in a column having a rectification zone and a stripping zone.

14. The method of claim 13, wherein the column has a feed location for introducing the olefin stream into the column such that the rectification zone is above the feed location and the stripping zone is below the feed location.

15. The method of claim 10, wherein the extractive distillation uses a polar extractant having an average boiling point of at least 100° F. (38° C.) at 1 atm.

16. The method of claim 10, wherein the first stream comprises not greater than 5 wt % $C_4+$ olefin and higher boiling point hydrocarbons, and the second stream comprises at least 60 wt % $C_4+$ olefin and higher boiling point hydrocarbons.

17. The method of claim 10, further comprising separating the ethylene from the first stream and polymerizing the separated ethylene to form polyethylene.

18. The method of claim 10, further comprising separating the propylene from the first stream and polymerizing the separated propylene to form polypropylene.

19. A method of removing dimethyl ether from an olefin stream made from an oxygenate to olefin reaction process, comprising:

contacting oxygenate with a molecular sieve catalyst to form an olefin stream, wherein the olefin stream comprises ethylene, propylene, dimethyl ether and $C_4+$ olefin and higher boiling point hydrocarbons;

separating the olefin stream into a first stream comprising the ethylene, propylene and dimethyl ether and a second stream comprising the $C_4+$ olefin and higher boiling point hydrocarbons; and separating the dimethyl ether present in the first stream using extractive distillation.

20. The method of claim 19, wherein the olefin stream is separated into the first and second streams using distillation.

21. The method of claim 19, wherein the ethylene is separated from the first stream prior to separating the dimethyl ether using the extractive distillation.

22. The method of claim 19, wherein the extractive distillation is carried out in a column having a rectification zone and a stripping zone.

23. The method of claim 22, wherein the column has a feed location for introducing the olefin stream into the column such that the rectification zone is above the feed location and the stripping zone is below the feed location.

24. The method of claim 19, wherein the extractive distillation uses a polar extractant having an average boiling point of at least 100° F. (38° C.) at 1 atm.

25. The method of claim 19, further comprising separating the ethylene from the first stream and polymerizing the separated ethylene to form polyethylene.

26. The method of claim 19, further comprising separating the propylene from the first stream and polymerizing the separated propylene to form polypropylene.

27. The method of claim 19, wherein the olefin stream further comprises not greater than 5 wt % methanol.

28. A method of removing dimethyl ether from an olefin stream made from an oxygenate to olefin reaction process, comprising:

contacting the oxygenate with a molecular sieve catalyst to form the olefin stream;

distilling the olefin stream to separate a propane and dimethyl ether containing stream from the olefin stream, wherein the propane and dimethyl ether containing stream comprises not greater than 5 wt % $C_4+$ olefin and higher boiling point hydrocarbons; and separating the dimethyl ether present in the propane and dimethyl ether containing stream using extractive distillation.

29. The method of claim 28, wherein the extractive distillation is carried out in a column having a rectification zone and a stripping zone.

30. The method of claim 29, wherein the column has a feed location for introducing the olefin stream into the column such that the rectification zone is above the feed location and the stripping zone is below the feed location.

31. The method of claim 28, wherein the extractive distillation uses a polar extractant having an average boiling point of at least 100° F. (38° C.) at 1 atm.

32. The method of claim 28, wherein the olefin stream further comprises not greater than 5 wt % methanol.

* * * * *